(12) United States Patent
Newman et al.

(10) Patent No.: US 8,119,642 B2
(45) Date of Patent: Feb. 21, 2012

(54) STRUCTURALLY RIGID DOPAMINE D3 RECEPTOR SELECTIVE LIGANDS AND PROCESS FOR MAKING THEM

(75) Inventors: Amy Newman, Phoenix, MD (US);
Peter Grundt, Baltimore, MD (US);
Robert R. Luedtke, Forth Worth, TX (US)

(73) Assignees: The United States of America as represented by the Secretary of the Department of Health and Human Services, Washington, DC (US);
University of North Texas Health Science Center at Fort Worth, Fort Worth, TX (US)

( * ) Notice: Subject to any disclaimer, the term of this patent is extended or adjusted under 35 U.S.C. 154(b) by 52 days.

(21) Appl. No.: 12/558,983

(22) Filed: Sep. 14, 2009

(65) Prior Publication Data

US 2010/0068138 A1    Mar. 18, 2010

Related U.S. Application Data

(62) Division of application No. 10/527,594, filed as application No. PCT/US03/28895 on Sep. 15, 2003, now Pat. No. 7,605,259.

(60) Provisional application No. 60/410,715, filed on Sep. 14, 2002.

(51) Int. Cl.
*A61K 31/4965* (2006.01)
*C07D 295/00* (2006.01)

(52) U.S. Cl. .................. 514/255.02; 544/393

(58) Field of Classification Search .................. None
See application file for complete search history.

(56) References Cited

U.S. PATENT DOCUMENTS

| | | |
|---|---|---|
| 5,143,923 A | 9/1992 | Hrib et al. |
| 5,958,923 A | 9/1999 | Hellendahl et al. |
| 6,124,294 A | 9/2000 | Hellendahl et al. |
| 6,342,604 B1 | 1/2002 | Hellendahl et al. |

FOREIGN PATENT DOCUMENTS

| | | |
|---|---|---|
| DE | 4 425 143 | 1/1996 |
| DE | 4 425 144 | 1/1996 |
| DE | 4 425 145 | 1/1996 |

OTHER PUBLICATIONS

Pilla, M. et al. Nature 400 371-375 (1999).
DiCiano, P. et al. Neuropsychopharmacology 28 329-338 (2003).
Yokoi F. et al., Neuropsychopharmacology 27 (2) 248-259 (2002).
Soares JC and Innis RB, Society of Biol Psychiatry 46(5) 600-615 (1999).
Huang et al. J. Med. Chem 44 1815-1826 (2001).
Luedtke et al. Synapse 38 438-449 (2000).
Videbaek C, J Cereb Blood Flow Metab 21 92-97 (2000).
Pilowsky L.S., Nucl Med Commun 22; 829-833 (2001).
Langer, Science 249 1527-1533 (1990).
Vorel, S.R. et al. J Neurosci 22 9595-9603 (2002).
Joyce, Pharmacol & Therapeutics 90 (2-3) 231-259 (2001).
Le Foll et al., Eur J Psychiatry vol. 15 140-146 (2000).
Newman et al. Biorganic and Medicinal Chemistry Letters, 2003, 13, 2179-83.

*Primary Examiner* — Noble Jarrell
(74) *Attorney, Agent, or Firm* — Cantor Colburn LLP (57) ABSTRACT

A family of structurally rigid dopamine D3 receptor selective ligands is described. The family of structurally rigid dopamine D3 receptor selective ligands has the formula wherein A is cis or trans —CH═CH—, —C≡C—, or cyclohexyl. B is cis or trans —CH═CH— or absent. R1 represents an optionally substituted phenyl group, wherein said substituents are selected from the group consisting of: hydrogen, halogen, amino, nitro, hydroxyl, alkoxy, alkyl, acyl and pyridyl, and said substitution may occur at any of the ortho, meta, or para positions, or R1 represents a heteroaromatic ring. A preferred heteroaromatic ring is indole, quinoxoline, pyridyl, pyrimidyl, or imidazole. R2 and R3 may be independently hydrogen or a halogen, or R2 alone may be C1, C2, or C3 alkoxy, and m is 1 or 2, and n is 0, 1, or 2.

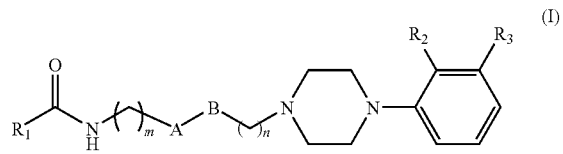

15 Claims, 1 Drawing Sheet

Figure 1. Synthesis of Rigid D₃ Ligands

STRUCTURALLY RIGID DOPAMINE D3 RECEPTOR SELECTIVE LIGANDS AND PROCESS FOR MAKING THEM

This application is a divisional of U.S. application Ser. No. 10/527,594, filed Dec. 13, 2005, issued as U.S. Pat. No. 7,605,259 on Oct. 20, 2009, which is a 371(e) National Phase application of PCT Application No. US 2003/028895, filed Sep. 15, 2003, which claims priority under 35 U.S.C. 119(e) from U.S. Provisional Application No. 60/410,715 filed on Sep. 14, 2002, each of which is hereby incorporated by reference in its entirety.

FIELD OF THE INVENTION

The present invention relates generally to a family of structurally rigid dopamine D3 receptor ligands. The family, of structurally rigid dopamine D3 receptor ligands have high affinity and selectivity for dopamine D3 receptors and may be used to treat psychostimulant abuse (e.g., cocaine, amphetamine and derivatives thereof), as well as other neuropsychiatric and neurodegenerative disorders (e.g., psychosis or Parkinson's disease, respectively). In addition, the present invention relates to the use of such structurally rigid dopamine D3 receptor ligands to image dopamine D3 receptor distribution in vivo, and to diagnose and/or monitor neurodegenerative disorders.

BACKGROUND OF THE INVENTION

The dopamine D3 receptor subtype is a member of the dopamine D2 subclass of receptors. These receptors have been implicated in a number of central nervous system (CNS) disorders including but not limited to psychostimulant abuse, psychosis and Parkinson's disease (Le Foll et al., *Eur J Psychiatry* 15:140-146 (2000); Joyce, *Pharmacol Ther* 90(2-3): 231-259 (2001)). Compounds that bind with high affinity and selectivity to D3 receptors can not only provide important tools with which to study the structure and function of this receptor subtype, but may also have therapeutic implications in these psychiatric and neurologic disorders.

Ger. Offen. DE 4,425,144 (equivalent to U.S. Pat. No. 6,124,294) discloses triazole compounds and their use for treating disorders which respond to dopamine D3 ligands. U.S. Pat. No. '294 fails to disclose any compounds that do not include a triazole ring. Thus all of the compounds of U.S. Pat. No. '294 are outside the scope of the present invention. Ger. Offen. DE 4,425,143 (equivalent to U.S. Pat. No. 6,342,604) discloses pyrimidine compounds and their use for treating disorders which respond to dopamine D3 ligands. U.S. Pat. No. '604 fails to disclose any compounds that do not include a thioether linkage. Thus all of the compounds of U.S. Pat. No. '604 are outside the scope of the present invention. Finally, Ger. Offen. DE 4,425,145 (equivalent to U.S. Pat. No. 5,958,923) discloses thiazole compounds and their use for treating disorders which respond to dopamine D3 ligands. U.S. Pat. No. '923 fails to disclose any compounds that do not include a thiazole ring. Thus, all of the compounds of U.S. Pat. No. '923 are considered to fall outside the scope of the present invention.

The compounds of the invention are useful as imaging agents (PET, SPECT) for D3 receptors in the central nervous system and have utility in diagnosis of disease states related to abnormal D3 receptor function or expression. Structurally rigid analogs provide selective and orally bioavailable drugs that are superior to currently available D3 receptor ligands. These compounds have therapeutic use in treating substance abuse, especially cocaine and amphetamine, psychosis, and Parkinson's disease.

DETAILED DESCRIPTION OF THE INVENTION

The present invention provides a family of structurally rigid dopamine D3 receptor ligands. More particularly, the present invention provides a family of structurally rigid dopamine D3 receptor ligands having the formula (I)

wherein A is cis or trans —CH=CH—, —CH≡CH—, or cyclohexyl. When A is cyclohexyl, the ring can be in chair or boat conformation.

B is cis or trans —CH=CH— or absent.

$R_1$ represents an optionally substituted phenyl ring, wherein said substituents are selected from the group consisting of: hydrogen, halogen, amino, nitro, hydroxyl, alkoxy, alkyl, acyl and pyridyl, and said substitution may occur at any of the ortho, meta, or para positions, or $R_1$ represents a heteroaromatic ring. A preferred heteroaromatic ring is indole, quinoxoline, pyridyl, pyrimidyl, or imidazole.

$R_2$ and $R_3$ may be independently hydrogen or a halogen, or $R_2$ alone may be $C_1$, $C_2$, or $C_3$ alkoxy, and m is 1 or 2, and n is 0, 1, or 2.

Even more particularly, the present invention provides a family of structurally rigid dopamine D3 receptor ligands having the formula (I)

wherein A is cis or trans —CH=CH—, —CH≡CH—, or cyclohexyl. When A is cyclohexyl, the ring can be in chair or boat conformation.

B is cis or trans —CH=CH— or absent.

$R_1$ represents an optionally substituted phenyl group with the exception that $R_1$ is not triazole or thiadiazole, wherein said substituents are selected from the group consisting of: hydrogen, halogen, amino, nitro, hydroxyl, alkoxy, alkyl, acyl and pyridyl, and said substitution may occur at any of the ortho, meta, or para positions, or $R_1$ represents a heteroaromatic ring. A preferred heteroaromatic ring is indole, quinoxoline, pyridyl, pyrimidyl, or imidazole. Optionally $R_1$ may also exclude pyrimidine.

$R_2$ and $R_3$ may be independently hydrogen or a halogen, or $R_2$ alone may be $C_1$, $C_2$, or $C_3$ alkoxy, and m is 1 or 2, and n is 0, 1, or 2.

Structure-Activity Relationships (SAR) developed by our laboratory and others demonstrated that the 2,3-dichloro-substituted or 2-methoxy-phenylpiperazine was optimal for high affinity binding at D3, wherein every compound with this substituent was more potent than its unsubstituted homologue. The optimum alkyl chain length, between the amido-aryl function and the phenylpiperazine was four carbons, when this linking chain was fully saturated. Although 5-carbon linked compounds exhibit reasonably high affinity for D3, D2 affinity was also very high, compromising the advantage of D3-selectivity. An amide-linked fluorenyl ring as $R_1$ was determined to be optimal when substituted at either the 2- or 4-positions. However, when a trans olefin was placed in the hydrocarbon linker between the amide group and the 2,3-dichlorophenylpiperazine, the fluorenyl ring could be replaced with the significantly less lipophilic phenyl ring. The addition of an alkene in the linker chain slightly shortens it and changes the shape of the molecule. Thus, longer chains (5-6 carbons) and/or an additional alkene provide an improved binding profile over the fully saturated compounds. Furthermore, replacing the phenyl ring with heteroaryl ring systems further reduced lipophilicity, while retaining or improving high D3 affinity and selectivity.

In Formula I, $R_2$ and $R_3$ are independently selected and are functional groups including, but not limited to, hydrogen, alkoxy, and halogen. The term "independently selected" is used herein to indicate that the two R groups, i.e., $R_2$ and $R_3$, can be identical or different (e.g., $R_2$ and $R_3$ may both be chloride atoms).

The term "alkyl" is used herein to refer to a branched or unbranched, saturated or unsaturated, monovalent hydrocarbon radical having from 1-8 carbons, cycloalkyls (3-7 carbons), cycloalkylmethyls (3-8 carbons) and arylalkyls. Suitable alkyl radicals include, for example, methyl, ethyl, n-propyl, propyl, 2-propenyl (or allyl), n-butyl, t-butyl, i-butyl (or 2-methylpropyl), cyclopropylmethyl, i-amyl, n-amyl, hexyl, etc. As used herein, the term alkyl encompasses "substituted alkyls." The term "substituted alkyl" refers to alkyl as just described including one or more functional groups such as lower alkyl, aryl, aralkyl, acyl, halogen (i.e., alkylhalos, e.g., $CF_3$), hydroxyl, amino, acylamino, acyloxy, alkoxyl, mercapto and the like. These groups may be attached to any carbon atom of the lower alkyl moiety.

The term "alkoxy" is used herein to refer to the —OR group, where R is a lower alkyl, substituted lower alkyl, aryl, substituted aryl, aralkyl or substituted aralkyl. Suitable alkoxy radicals include, for example, methoxy, ethoxy, phenoxy, t-butoxy, etc.

The term "lower alkyl" means $C_1$ to $C_3$.

The term "aryl" refers to an aromatic substituent which may be a single ring or multiple rings which are fused together, linked covalently, or linked to a common group such as an ethylene or methylene moiety. The aromatic ring(s) may include phenyl, naphthyl, biphenyl, diphenylmethyl, 2,2-diphenyl-1-ethyl, and may contain a heteroatom, such as thienyl, pyridyl and quinoxalyl. The aryl group may also be substituted with halogen atoms, or other groups such as nitro, carboxyl, alkoxy, phenoxy, and the like. Additionally, the aryl group may be attached to other moieties at any position on the aryl radical which would otherwise be occupied by a hydrogen atom (such as 2-pyridyl, 3-pyridyl and 4-pyridyl). As such, the terms "arylalkyl" and "aryloxyalkyl" refer to an aryl radical attached directly to an alkyl group (e.g., 3(2-pyridyl) propyl)) or an oxygen which is attached to an alkyl group, respectively.

The term "acyl" is used herein to refer to the group —C(O)R, where R is hydrogen, alkyl or substituted alkyl, aryl, or substituted aryl as defined above.

The term "cyano" is used herein to refer to the group —CN.

The term "halogen" is used herein to refer to fluorine, bromine, chlorine, and iodine atoms.

The term "hydroxyl" is used herein to refer to the group —OH.

The term "nitro" is used herein to refer to the —$NO_2$ group.

The term "amino" is used herein to refer to the group NRR', where R and R' may independently be hydrogen, lower alkyl, substituted lower alkyl, aryl, substituted aryl or acyl.

Within the scope of formula I, certain embodiments are preferred, namely a compound having the formula II:

or the formula III:

or the formula IV, wherein the carbon chain linker is in cis configuration:

In formulas II, III, and IV, $R_1$ and A are the same as defined above. Other preferred compounds are presented in Table 1, below.

Based on their neurochemical and behavioral properties, the structurally rigid dopamine D3 receptor selective ligands of the present invention are useful as therapeutics for the treatment of psychostimulant abuse, such as cocaine, amphetamine and derivatives thereof.

It should be noted that dopamine D3 selective agents are preferred over nonselective D2/D3 receptor ligands or dopamine transporter ligands for the treatment of psychostimulant abuse, as they will not demonstrate a cocaine-like behavioral profile or have abuse potential. Furthermore, the structurally rigid dopamine D3 ligands of the present invention will not have other negative (extrapyramidal) side effects associated with the dopamine D2 class of therapeutic agents (ex. Haloperidol). Furthermore, dopamine D3 receptor antagonists have been shown, in animal models, to extinguish cocaine-seeking behavior and thus will be useful in reducing craving.

As such, in another aspect, the present invention provides a method of treating psychostimulant abuse in a subject, the method comprising administering to the subject a therapeutically effective amount of a compound disclosed herein.

As used herein, "psychostimulant abuse" has its conventional meaning, i.e., misuse or addiction of a psychostimulant, such as cocaine, amphetamine and derivatives thereof. Typically, cocaine is taken by a person due to a craving for cocaine generated by its prior use. Cocaine is abused when it is used for gratification, producing effects not required or recommended for therapy. The resultant high use of cocaine produces many serious and adverse side effects. As such, it is highly desirable to reduce the number and/or intensity of episodes in which a person experiences a craving for the substance or, more preferably, to eliminate the craving episodes entirely. Dopamine D3 antagonists or partial agonists have demonstrated utility in reducing craving in animal models (Pilla, M. et al. *Nature* 400:371-375 (1999), Vorel, S. R. et al. *J. Neurosci.* 22:9595-9603 (2002), DiCiano, P. et al. *Neuropsychopharmacology* 28:329-338 (2003)).

"Treatment" or "treating," as used herein, refers to any administration of a compound of the present invention and includes: (i) inhibiting the symptoms of the disease, e.g., cocaine addiction; and/or (ii) lessening or inhibiting the long term effects of the disease, e.g., cocaine addiction. In therapeutic applications, compositions are administered to a patient already suffering from the disease, e.g., cocaine addiction or Parkinson's disease, in an amount sufficient to cure or at least partially arrest the symptoms of the disease and its complications. An amount adequate to accomplish this is defined as a "therapeutically effective amount or dose." Amounts effective for this use will depend on the severity and course of the disease, previous therapy, the patient's health status and response to the drugs, and the judgment of the treating physician.

In conjunction with the foregoing method, the present invention provides pharmaceutical compositions comprising a compound disclosed herein and a pharmaceutically acceptable diluent, carrier or excipient. While it is possible to administer the active ingredient of this invention alone, it is preferable to present it as part of a pharmaceutical formulation. The formulations of the present invention comprise at least one compound described herein in a therapeutically or pharmaceutically effective dose together with a pharmacologically or therapeutically acceptable carrier. The phrase "pharmaceutically or therapeutically acceptable carrier," as used herein, refers to a carrier medium which does not interfere with the effectiveness of the biological activity of the active ingredients and which is not toxic to the host or patient.

The pharmaceutical compositions of the present invention can be in a variety of forms. These include, for example, solid, semi-solid and liquid dosage forms, such as tablets, pills, powders, liquid solutions or suspensions, liposomes, injectable and infusible solutions. Inhalable preparations, such as aerosols, are also included. Preferred formulations are those directed to oral, intranasal and parenteral applications, but it will be appreciated that the preferred form will depend on the particular therapeutic application at hand. The methods for the formulation and preparation of therapeutic compositions comprising the compounds of the invention are well known in the art and are described in, for example, REMINGTON'S PHARMACEUTICAL SCIENCES (Mack Publishing Company, Philadelphia, Pa., 17th ed. (1985)), THE MERCK INDEX 11th Ed., (Merck & Co. 1989), and Langer, Science 249: 1527-1533 (1990), the teachings of which are incorporated herein by reference.

For parenteral administration, for example, the pharmaceutical compositions comprise a solution of a compound of the present invention, as described above, dissolved or suspended in an acceptable carrier, preferably an aqueous carrier. A variety of aqueous carriers can be used including, for example, water, buffered water, 0.4% saline, 0.3% glycine, hyaluronic acid and the like. These compositions may be sterilized by conventional, well-known sterilization techniques or, they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, wetting agents and the like, such as, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally about 10% to about 95% of the active ingredient and, more preferably, about 25% to about 75% of the active ingredient.

For aerosol administration, the compounds of the present invention are preferably supplied in a finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included as desired, as with, e.g., lecithin, for intranasal delivery.

Once improvement of the patient's conditions has occurred, a maintenance dose is administered if necessary. Subsequently, the dosage or the frequency of administration, or both, can be reduced, as a function of the symptoms, to a level at which the improved condition is retained. When the symptoms have been alleviated to the desired level, treatment can cease. Patients can, however, require intermittent treatment on a long-term basis upon any recurrence of the disease symptoms.

In general, a suitable effective dose of the compounds of the present invention will be in the range of 0.05 to 1000 milligram (mg) per recipient per day, preferably in the range of 0.1 to 100 mg per day. The desired dosage is preferably presented in one, two, three, four or more subdoses administered at appropriate intervals throughout the day. These subdoses can be administered as unit dosage forms, for example, containing 0.01 to 1000 mg, preferably 0.01 to 100 mg of active ingredient per unit dosage form. Again, the desired dosage will depend on, for example, the particular compound employed, the disease to be treated, the manner of administration, the weight and general state of health of the patient, and the judgment of the prescribing physician.

Moreover, based on their neurochemical and behavioral properties, the structurally rigid D3 receptor selective ligands of the present invention are useful as imaging probes for dopamine D3 receptors and as imaging probes for neurodegenerative disorders (e.g., Parkinson's disease). As such, in another aspect, the present invention provides a method of selectively imaging dopamine binding sites of the central nervous system of a subject, such as the brain of a human patient, the method comprising:

(a) administering to the human an inventive compound of the present invention; and (b) detecting the binding of the compound to the central nervous system tissue, such as the dopamine D3 receptors in the brain.

Moreover, in yet another aspect, the present invention provides a method for detecting or monitoring a disease resulting from abnormal distribution and/or density of dopamine D3 receptor in the central nervous system of a subject, comprising:

(a) administering to the subject a detectably labeled compound of the invention;

(b) detecting the binding of that compound to dopamine D3 receptor in the central nervous system tissue;

(c) determining the distribution and/or density of the dopamine D3 receptor in the central nervous system tissue;

(d) comparing the distribution and/or density obtained in (c) with the distribution and/or density of dopamine D3 receptor in a corresponding normal tissue; and (e) diagnosing a disease state by a difference in the distribution and/or density between the normal tissue and the subject tissue.

In a presently preferred embodiment, the structurally rigid dopamine selective ligands of the present invention are labeled with a radioactive label using standard labeling techniques known to and used by those of skill in the art. Suitable labels include, but are not limited to: $^{123}$I, $^{11}$C, $^{18}$F, or $^{99}$Tc. In addition, binding of the dopamine D3 receptor selective ligands to the brain, such as limbic brain regions, including the islands of Calleja, is detected using methods known in the art, such as positron emission tomography (PET) or single-photon emission computed tomography (SPECT). (See, e.g., Yokoi F. et al., *Neuropsychopharmacology* 27(2):248-59 (2002); Pilowsky L. S., *Nucl Med Commun* 22(7):829-33 (2001); Soares J C and Innis R B, *Biol Psychiatry* 46(5):600-15 (1999); and Videbaek C, *J Cereb Blood Flow Metab* 21(1): 92-7 (2001), the teachings of which are incorporated herein by reference). Preferably SPECT imaging employs gamma-emitting derivatives of the ligands described herein (e.g., dopamine D3 receptor selective ligands labeled with $^{123}$I or $^{99}$Tc). Yokoi et al. (supra) have mapped the normal distribution of dopamine D2 and D3 receptors in humans. Using this method, one can diagnose and/or monitor neurodegenerative disorders, such as Parkinson's disease, characterized by the progressive degeneration of dopamine nerve terminals.

The invention will be described in greater detail by way of specific examples. The following examples are offered for illustrative purposes, and are intended neither to limit nor define the invention in any manner.

EXAMPLES

Figure 1:
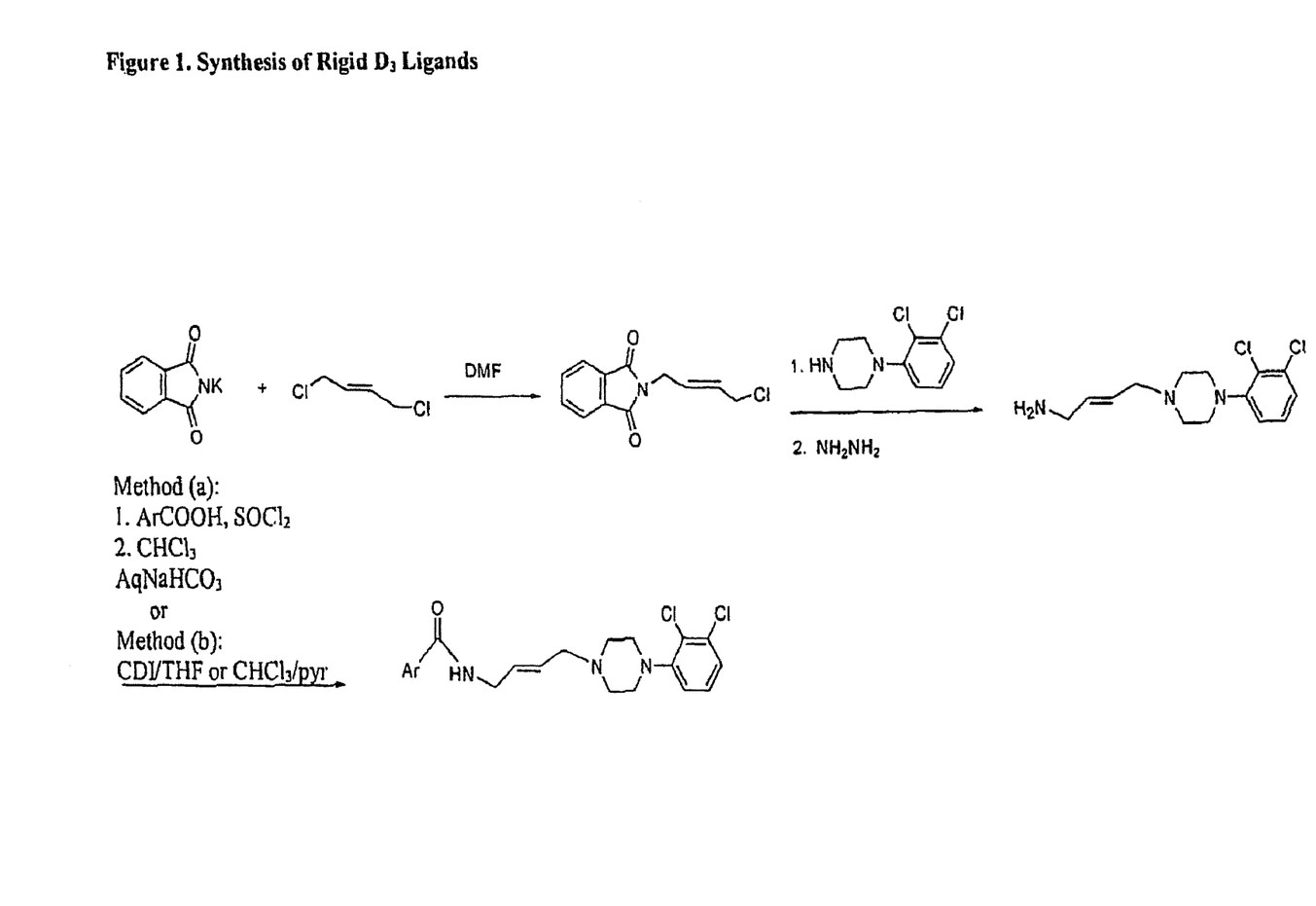
FIG. 1 illustrates the synthetic scheme used to prepare the structurally rigid dopamine D3 receptor selective ligands of the present invention.

The compounds of the present invention can be prepared using the synthetic scheme set forth in FIG. 1. In general, potassium phthalimide is reacted with the dihalo-butene (e.g., trans-1,4-dichloro-2-butene) or dihalo-cyclohexane in aprotic solvent (e.g., dimethylformamide). The resulting intermediate is then reacted with the appropriately substituted phenyl piperazine (e.g., 2,3-dichlorophenyl-piperazine) to give the N-protected intermediate which is then deprotected with hydrazine to give the desired phenyl-piperazino-amine (e.g., but-2-enyl). Reaction with the appropriately substituted aryl-carboxylic acid chloride, under biphasic conditions gives the desired amido-products.

Example 1

The following example illustrates synthesis of a specific compound disclosed herein. Steps 1-4 illustrate the synthetic steps to form the desired phenyl-piperazino-amine. Step 4 illustrates the synthetic step to form the desired amido end product.

Step 1: 2-(4-Chloro-but-2-enyl)-isoindole-1,3-dione

Trans-1,4-dichloro-2-butene (1.14 ml, 10.8 mmol) was dissolved in DMF (27 ml) and purged with argon. Potassium pthalamide (1.00 g, 5.40 mmol) was added to the solution and the reaction was allowed to stir at room temperature overnight. The reaction was then poured into water (75 ml), which precipitated a white solid. This solid was collected by filtration and purified using silica gel chromatography (3:1 Hex: EtOAc) to afford a 76% yield (961 mg) of a white solid.

Step 2: 2-{4-[4-(2,3-Dichloro-phenyl)-piperazin-1-yl]-but-2-enyl}-isoindole-1,3-dione A suspension of 4-(2,3-dichloro-phenyl)-piperazine (7.55 g, 32.8 mmol), 2-(4-trans-chloro-but-2-enyl)-isoindole-1,3-dione (7.73 g, 32.8 mmol) and sodium bicarbonate (13.7 g, 161 mmol) in acetonitrile (100 ml) was heated to 80° C. under an atmosphere of argon for 5 h. After that time, most of the inorganic salts were removed by filtration of the hot reaction mixture. The title compound crystallized out of the filtrate and was taken up in a minimum amount of chloroform. After filtration and evaporation of the solvent, 10.9 g (77%) was obtained as a solid.

Step 3: 4-[4-(2,3-Dichloro-phenyl)-piperazin-1-yl]-but-2-enylamine

To a solution of 2-{4-[4-(2,3-Dichloro-phenyl)-piperazin-1-yl]-but-2-enyl}-isoindole-1,3-dione (5.12 g, 11.9 mmol) in absolute ethanol (100 ml) under an atmosphere of argon was added hydrazine (0.75 ml, 24 mmol), and the reaction mixture was refluxed for 2.5 h. The ice-cold reaction mixture was filtered and solvent was removed under reduced pressure. The residue was purified by column chromatography to yield 2.63 g (74%) as yellow oil.

Step 4: Amidation Reaction—Representative Examples

Method (a): N-{4-[4-(2,3-Dichloro-phenyl)-piperazin-1-yl]-but-2-enyl}-4-iodo-benzamide (EEC 17)

4-Iodobenzoic acid (456 mg, 3.00 mmol) was refluxed with thionyl chloride (3 ml) for three hours. Excess thionyl chloride was removed by distillation followed by addition and distillation of dry toluene (3×5 ml) to give the acid chloride, which was used in the amidation reaction without further purification. A solution of the acid chloride (0.21 g, 0.83 mmol) in amylene stabilized chloroform (1.4 ml) was added slowly at 0° C. to an emulsion of 4-[4-(2,3-Dichloro-phenyl)-piperazin-1-yl]-but-2-enylamine (0.25 g, 0.83 mmol), amylene stabilized chloroform (8.3 ml), sodium bicarbonate (0.42 g, 5.0 mmol) and water (4.2 ml). The reaction mixture was allowed to stir at room temperature for 1 hour and after that time the aqueous layer was extracted with chloroform (3×5 ml). The organic layer was then washed once with water, dried with magnesium sulfate, filtered and evaporated to dryness. The residue was purified by recrystallization of its oxalic acid salt.

$^1$H NMR (CDCl$_3$) δ 2.62 (m, 4H), 3.04-3.06 (m, 6H), 4.06 (m, 2H), 5.75 (m, 2H), 6.50 ("t", "J" 5.4 Hz, 1H), 6.94 (dd, J 6.1, 3.5 Hz, 1H), 7.15 (m, 2H), 7.50 (d, J 8.5 Hz, 2H), 7.76 (d, J 8.5 Hz, 2H).

$^{13}$C NMR (CDCl$_3$): δ 40.43, 50.12, 52.09, 59.07, 97.36, 117.49, 123.46, 126.35, 127.46, 128.04, 128.34, 132.66, 132.86, 136.60, 150.06, 165.41.

IR (film): ν 1642, 1584.

Method (b): N-{4-[4-(2,3-Dichloro-phenyl)-piperazin-1-yl]-but-2-enyl}-4-hydroxy-benzamide (PG01015)

1,1'-carbonyldiimidazole (0.18 g, 1.1 mmol) was added to a solution of the 4-hydroxy benzoic acid (0.15 g, 1.1 mmol) in absolute pyridine and the mixture was stirred at room temperature under Argon for 1 h. After that time a solution of 4-[4-(2,3-Dichloro-phenyl)-piperazin-1-yl]-but-2-enylamine (0.33 g, 1.1 mmol) in 3 ml amylene-stabilized chloroform was added and the mixture was stirred overnight. All volatiles were removed in vacuo and the residue was purified by chromatography to give 0.23 g (51%) of the title compound.

$^1$H NMR (CDCl$_3$): δ 2.69 (m, 4H), 3.05-3.08 (m, 6H), 4.01 (m, 2H), 5.70-5.75 (m, 2H), 6.67 (t, J 5.5, 1H), 6.76 (d, J 8.6, 2H), 6.88 (m, 1H), 7.07-7.19 (m, 2H), 7.56 (d, J 8.6, 2H).

$^{13}$C NMR (CDCl$_3$): δ 41.23, 50.62, 53.00, 60.01, 115.60, 118.65, 124.75, 124.93, 126.66, 127.35, 127.51, 129.00, 131.27, 133.93, 150.74, 160.43, 167.71.

IR (film): ν 3309, 1633.

Example 2

The following example shows the calculation of the clogD values.

Calculation of the clogD values has provided guidance towards the design of molecules that are both able to cross the blood brain barrier and have appropriate biophysical properties for medication development (Table 1). cLOGD values were computed using the software ACD/LOGD suite. These values represent partition coefficients, as measure of lipophilicity, and were calculated at physiological pH of 7.4. The optimal range for medication development is 2-5. Molecular modeling has also been employed to identify which chemical moieties of previously active molecules are required for D3 selectivity.

Human dopamine D2-long ("D$_2$") and D3 ("D$_2$") receptors were expressed in HEK cells. In brief, stably transfected HEK cells expressing the human D2-long and the D3 dopamine receptor were developed using the pIRES bicistronic expression vector (CLONTECH; Palo Alto, Calif.). The level of expression of D2 or D3 receptors was determined to be greater than 2,000 fmoles/mg protein. For comparison, human dopamine D4 ("D$_4$") receptors were obtained from HEK 293 cells stably transfected with a PCR product o'f a human cDNA coding for the D4.4 form of the human D4 dopamine receptor. The density of binding sites is approximately 1000 fmol/mg protein.

Methods for performing in vitro dopamine receptor binding studies are described in Huang et al. *J. Med. Chem.* 44:1815-1826 (2001) and Luedtke et al. *Synapse* 38:438-439 (2000), the contents of which are hereby incorporated by reference. In brief, radioactively labeled dopamine selective ligands bind with picomolar affinity and nonselectivity to D$_2$ and D$_3$ dopamine receptors expressed in Sf9 and HEK 293 cells. $^{125}$I-IABN binds with 7- to 10-fold lower affinity to human D4.4 dopamine receptors expressed in HEK 293 cells. Dissociation constants (Kd) calculated from kinetic experiments were found to be in agreement with equilibrium Kd values obtained from saturation binding studies. Saturation plots of the binding of $^{125}$I-IABN with rat caudate membrane preparations were monophasic and exhibited low nonspecific binding. The pharmacologic profile of the binding of $^{125}$I-IABN to rat caudate was found to be consistent with a D$_2$-like receptor, suggesting that in the caudate the ligand binds primarily to D$_2$ dopamine receptors. IABN was found to bind with low affinity to sigma σ1 and σ2 binding sites, as well as to D$_{1a}$ dopamine receptors. Quantitative autoradiographic studies using rat brain indicated that $^{125}$I-IABN selectively labels the striatum and the olfactory tubercle area, which is consistent with the labeling receptors expressed in HEK cells. Therefore, $^{125}$I-IABN appears to be a high affinity, selective antagonist at D$_2$-like dopamine receptors.

Table 1 shows preferred compounds of the invention having the formula II, wherein R$_1$ and A are defined as below. The compounds were prepared according to the method described in Example 1, and the amidation reaction of step 4 was carried out via method (a) or method (b), as noted. The clogD values were determined in accordance with Example 2. Table 2 shows binding data in cloned human D3, D2, and D4 receptors in HEK cells.

TABLE 1

Synthetic methods and formulas of preferred D3 ligands

| Compd | R$_1$ | A | Method | Formula | clogD |
|---|---|---|---|---|---|
| PG01014 | 2-F-phenyl | CH=CH | a | C$_{21}$H$_{22}$Cl$_2$FN$_3$O•2HCl | 4.64 |
| PG01011 | 3-F-phenyl | CH=CH | a | C$_{21}$H$_{22}$Cl$_2$FN$_3$O•HCl•0.25H$_2$O | 5.31 |
| PG01012 | 4-F-phenyl | CH=CH | b | C$_{21}$H$_{22}$Cl$_2$FN$_3$O•1.5HCl•H$_2$O | 5.74 |

TABLE 1-continued

Synthetic methods and formulas of preferred D3 ligands

| Compd | R₁ | A | Method | Formula | clogD |
|---|---|---|---|---|---|
| PG01009 |  |  | a | $C_{21}H_{22}Cl_3N_3O \cdot HCl \cdot 1.25H_2O$ | 5.18 |
| EEC 063 |  |  | a | $C_{21}H_{22}Cl_3N_3O \cdot (COOH)_2 \cdot CH_3COCH_3$ | 5.86 |
| PG01007 |  |  | a | $C_{21}H_{22}Cl_3N_3O \cdot HCl \cdot 0.5H_2O$ | 5.77 |
| PG01018 |  |  | b | $C_{21}H_{22}Cl_2IN_3O \cdot HCl \cdot H_2O$ | 5.62 |
| EEC 019 |  |  | a | $C_{21}H_{22}Cl_2IN_3O \cdot (COOH)_2$ | 6.31 |
| EEC 017 |  |  | a | $C_{21}H_{22}Cl_2IN_3O \cdot (COOH)_2$ | 6.21 |
| PG01027 |  |  | a | $C_{22}H_{25}Cl_2N_3O_2 \cdot (CHCOOH)_2 \cdot 0.5H_2O$ | 4.82 |
| EEC 069 |  |  | a | $C_{22}H_{25}Cl_2N_3O_2 \cdot (CHCOOH)_2 \cdot 0.5H_2O$ | 4.65 |
| EEC 067 |  |  | a | $C_{22}H_{25}Cl_2N_3O_2 \cdot (COOH)_2 \cdot H_2O$ | 5.18 |
| PG01025 |  |  | b | $C_{21}H_{23}Cl_2N_3O_2 \cdot 2HCl$ | 5.31 |
| PG01015 |  |  | b | $C_{21}H_{23}Cl_2N_3O_2 \cdot 2HCl \cdot 0.5H_2O$ | 4.61 |

TABLE 1-continued

Synthetic methods and formulas of preferred D3 ligands

| Compd | R₁ | A | Method | Formula | clogD |
|---|---|---|---|---|---|
| PG01029 |  |  | a | $C_{21}H_{22}Cl_2N_4O_3 \cdot HCl \cdot 1.5H_2O$ | 5.29 |
| PG01013 |  |  | a | $C_{21}H_{22}Cl_2N_4O_3 \cdot 2HCl$ | 4.92 |
| EEC 027 |  |  | a | $C_{21}H_{22}Cl_2N_4O_3 \cdot 2(COOH)_2 \cdot 1.5H_2O$ | 5.17 |
| PG01038 |  |  | b | $C_{21}H_{24}Cl_2N_4O \cdot 2HCl \cdot H_2O$ | 4.77 |
| PG01026 |  |  | b | $C_{21}H_{24}Cl_2N_4O \cdot 3HCl \cdot 0.33CHCl_3$ | 4.04 |
| PG01034 |  |  | a | $C_{20}H_{22}Cl_2N_4O \cdot 3HCl$ | 3.93 |
| PG01022 |  |  | a | $C_{20}H_{22}Cl_2N_4O \cdot 3HCl \cdot 1.25H_2O$ | 4.15 |
| PG01035 |  |  | a | $C_{20}H_{22}Cl_2N_4O \cdot 3HCl \cdot 0.5H_2O$ | 3.75 |
| PG01020 |  |  | b | $C_{23}H_{23}Cl_2N_5O \cdot (COOH)_2 \cdot 0.25H_2O$ | 4.92 |
| PG01055 |  |  | b | $C_{23}H_{23}Cl_2N_3O_2 \cdot HCl \cdot H_2O$ | 5.86 |
| PG01030 |  |  | a | $C_{23}H_{23}Cl_2N_3OS \cdot (COOH)_2$ | 7.10 |
| PG01037 |  |  | b | $C_{26}H_{26}Cl_2N_4O \cdot 2HCl \cdot 3H_2O$ | 5.31 |

TABLE 1-continued

Synthetic methods and formulas of preferred D3 ligands

| Compd | R₁ | A | Method | Formula | clogD |
|---|---|---|---|---|---|
| PG01041 |  |  | b | $C_{26}H_{26}Cl_2N_4O \cdot (COOH)_2 \cdot 2H_2O$ | 5.34 |
| JJC 2-069 |  |  | b | $C_{28}H_{27}Cl_2N_3O(COOH)_2 \cdot 1.5H_2O$ | 7.07 |
| JJC 2-084 |  |  | b | $C_{28}H_{27}Cl_2N_3O \cdot (COOH)_2 \cdot 0.5H_2O$ | 7.07 |
| JJC 2-071 |  |  | b | $C_{28}H_{27}Cl_2N_3O \cdot (COOH)_2 \cdot 0.25H_2O$ | 7.07 |
| JJC 2-085 |  |  | b | $C_{28}H_{27}Cl_2N_3O \cdot (COOH)_2 \cdot 0.5H_2O$ | 7.07 |
| JJC 2-068 |  |  | a | $C_{21}H_{23}Cl_2N_3O \cdot (COOH)_2 \cdot 0.5H_2O$ | 5.13 |
| JJC 2-083 |  |  | a | $C_{21}H_{23}Cl_2N_3O \cdot HCl$ | 5.13 |
| JJC 2-077 |  |  | b | $C_{28}H_{25}Cl_2N_3O \cdot (COOH)_2 \cdot 0.25H_2O$ | 7.04 |
| JJC 2-078 |  |  | b | $C_{28}H_{25}Cl_2N_3O \cdot (COOH)_2$ | 7.04 |
| JJC 2-062 |  |  | a | $C_{21}H_{21}Cl_2N_3O \cdot (COOH)_2$ | 5.10 |

TABLE 2

Binding data in cloned human $D_2$, $D_3$ and $D_4$ receptors in HEK cells

| Compound | $D_2$ | $D_3$ | $D_4$ | $D_2/D_3$ |
|---|---|---|---|---|
| PG01014 | 10.1 ± 1.9 | 1.2 ± 0.1 | n.d. | 8 |
| PG01011 | 8.8 ± 0.7 | 1.7 ± 0.4 | n.d. | 5 |
| PG01012 | 8.1 ± 2.7 | 1.0 ± 0.2 | n.d. | 8 |
| PG01009 | 13.1 ± 5.5 | 1.3 ± 0.2 | n.d. | 10 |
| EEC 063 | 15.0 ± 2.8 | 2.1 ± 1.1 | n.d. | 7 |
| PG01007 | 25.0 ± 10.8 | 1.6 ± 1.0 | n.d. | 16 |
| PG01018 | 12.7 ± 4.1 | 3.8 ± 0.6 | n.d. | 3 |
| ECC 019 | 28.1 ± 3.0 | 3.9 ± 1.2 | n.d. | 7 |
| EEC 017 | 35.4 ± 7.6 | 4.2 ± 1.5 | n.d. | 8 |
| PG01027 | 5.3 ± 3.0 | 0.6 ± 0.1 | n.d. | 9 |
| EEC 069 | 56.9 ± 19.1 | 4.0 ± 1.6 | n.d. | 14 |
| EEC 067 | 34.7 ± 11.4 | 1.2 ± 0.2 | n.d. | 29 |
| PG01025 | 7.3 ± 3.2 | 0.8 ± 0.2 | n.d. | 9 |
| PG01015 | 13.7 ± 4.8 | 0.4 ± 0.0 | 356.3 ± 26.5 | 34 |
| PG01029 | 10.5 ± 4.5 | 3.4 ± 0.7 | n.d. | 3 |
| PG01013 | 21.9 ± 4.0 | 2.3 ± 0.5 | n.d. | 10 |
| EEC 027 | 19.7 ± 3.6 | 0.6 ± 0.2 | 460.6 ± 187 | 33 |
| PG01038 | 25.6 ± 6.8 | 2.7 ± 0.8 | n.d. | 9 |
| PG01026 | 29.0 ± 9.4 | 2.0 ± 0.4 | n.d. | 14 |
| PG01034 | 31.2 ± 3.1 | 2.0 ± 0.6 | n.d. | 16 |
| PG01022 | 11.2 ± 5.6 | 2.2 ± 0.6 | n.d. | 5 |
| PG01035 | 17.2 ± 4.2 | 3.7 ± 0.9 | n.d. | 5 |
| PG01020 | 70.0 ± 7.6 | 3.7 ± 0.8 | 1114 ± 555 | 19 |
| PG01055 | 100.9 ± 16.9 | 2.8 ± 0.6 | 1065 ± 382 | 36 |
| PG01030 | 148.7 ± 9.7 | 1.3 ± 0.5 | 1771 ± 390 | 114 |
| PG01037 | 81.9 ± 20.7 | 0.7 ± 0.1 | 504.8 ± 62.5 | 117 |
| PG01041 | 63.3 ± 16.5 | 0.7 ± 0.1 | 485.6 ± 157 | 90 |
| JJC 2-069 | 62.9 ± 12.7 | 8.2 ± 2.3 | n.d. | 8 |
| JJC 2-084 | 8.1 ± 1.6 | 1.2 ± 0.5 | n.d. | 7 |
| JJC 2-071 | 185.6 ± 8 | 3.4 ± 2.9 | n.d. | 55 |
| JJC 2-085 | 61.1 ± 19.2 | 3.8 ± 1.4 | n.d. | 16 |
| JJC 2-068 | 2.9 ± 1 | 0.6 ± 0.1 | n.d. | 5 |
| JJC 2-083 | 2.5 ± 0.9 | 0.4 ± 0.1 | n.d. | 6 |
| JJC 2-077 | 592 ± 27 | 318 ± 32 | n.d. | 2 |
| JJC 2-078 | 1650 ± 692 | 41.5 ± 5.4 | n.d. | 40 |
| JJC 2-062 | 491 ± 108 | 127 ± 10 | n.d. | 4 |

Example 3

Functional data on preferred compounds of the invention demonstrating D3 antagonism.

To measure D2 and D3 stimulation of mitogenesis (agonist assay) or D2 and D3 inhibition of quinpirole stimulation of mitogenesis (antagonist assay), CHOp-cells (human receptor) were seeded in a 96-well plate at a concentration of 5,000 cells/well. The cells were incubated at 37° C. in α-MEM with 10% FBS, 0.05% penicillin-streptomycin, and 200 µg/mL of G418. After 48 hours, the cells were rinsed twice with serum-free α-MEM and incubated for 24 hours at 37° C. In the functional assay for agonism, the medium was removed and replaced with 90 µl of serum-free α-MEM and 10 µl of test compound in sterile water; in the antagonist assay, the test compound was diluted in sterile water plus 30 nM quinpirole. After another 24-hour incubation at 37° C., 0.25 µCi of [$^3$H] thymidine was added to each well and the plates were further incubated for 2 hours at 37° C. The cells were then trypsinized, and the plates were filtered and counted as usual in the art. Quinpirole was run on every plate as an internal standard.

TABLE 3

$D_3$ Functional Assay using Stimulation or Inhibition of Quinpirole Stimulation of Mitogenesis in CHO cells ($hD_3$)

| Compound | Agonist $EC_{50}$ (nM) ± S.E.M. | % Max Stim. ± S.E.M. | Antagonist $IC_{50}$ (nM) ± S.E.M. |
|---|---|---|---|
| JJC 2071 | 173 ± 9.6 | 44.1 ± 0.9 | — |
| JJC 2-068 | >10,000 | — | 7.72 ± 1.6 |
| JJC 2-083 | >10,000 | — | 6.00 ± 0.59 |
| JJC 2-069 | >10,000 | — | 114.60 ± 31.68 |

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

We claim:

1. A compound having the formula (I)

wherein
A is cis or trans —CH═CH—;
B is cis or trans —CH═CH— or absent;
$R_1$ represents an optionally substituted phenyl group, wherein said substituents are selected from the group consisting of: hydrogen, halogen, amino, nitro, hydroxyl, alkoxy, alkyl, acyl and pyridyl, and said substitution may occur at any of the ortho, meta, or para positions;
$R_2$ and $R_3$ is each independently hydrogen or a halogen, or $R_2$ alone is $C_1$, $C_2$, or $C_3$ alkoxy;
m is 1 or 2; and
n is 0, 1, or 2.

2. A compound having the formula (I)

wherein
A is cis or trans —CH═CH—;
B is cis or trans —CH═CH— or absent;
$R_1$ represents an optionally substituted phenyl group, wherein said substituents are selected from the group consisting of: hydrogen, halogen, amino, nitro, hydroxyl, alkoxy, alkyl, acyl and pyridyl;
$R_2$ and $R_3$ may be independently hydrogen or a halogen;
m is 1 or 2; and
n is 0, 1, or 2.

3. The compound of claim 1, wherein B is absent, $R_2$ and $R_3$ are both halogen, m is 1 and n is 1.

4. The compound of claim 1, wherein B is absent, $R_2$ is lower alkoxy, $R_3$ is H, m is 1 and n is 1.

5. The compound of claim 1, wherein $R_1$ is phenyl substituted by a halogen, an amino group, a nitro group, a methoxy group, or pyridyl group.

6. A compound having the formula:

wherein

A is cis or trans —CH═CH—; and $R_1$ represents an optionally substituted phenyl group, wherein said substituents are selected from the group consisting of: hydrogen, halogen, amino, nitro, hydroxyl, alkoxy, alkyl, acyl and pyridyl, and said substitution may occur at any of the ortho, meta, or para positions, or $R_1$ represents a heteroaromatic ring, with the exception that $R_1$ is not triazole or thiadiazole.

7. A method for selectively imaging dopamine D3 receptor in the central nervous system of a subject, comprising:

(a) administering a radioactively labeled compound of claim 1 to the subject; and (b) detecting the binding of that compound to dopamine D3 receptors in the central nervous system of the subject.

8. The method of claim 7, wherein the central nervous system tissue is brain tissue.

9. A compound having the formula wherein

A is cis or trans —CH═CH—;

B is absent;

$R_1$ represents optionally substituted phenyl group, wherein said substituents are selected from the group consisting of: hydrogen, halogen, amino, nitro, hydroxyl, alkoxy, alkyl, acyl and pyridyl, and said substitution may occur at any of the ortho, meta, or para positions;

$R_2$ and $R_3$ is each independently hydrogen or a halogen, or $R_2$ alone is $C_1$, $C_2$, or $C_3$ alkoxy;

m is 1 or 2; and n is 0, 1, or 2.

10. A pharmaceutical composition comprising a compound of claim 9 and a pharmaceutically acceptable diluent, carrier or excipient.

11. A compound having the formula wherein

A is trans —CH═CH—;

B is cis or trans —CH═CH— or absent;

$R_1$ represents an substituted phenyl group, wherein said substituents are selected from the group consisting of: hydrogen, halogen, amino, nitro, hydroxyl, alkoxy, alkyl, acyl and pyridyl, and said substitution may occur at any of the ortho, meta, or para positions;

$R_2$ and $R_3$ is each independently hydrogen or a halogen, or $R_2$ alone is $C_1$, $C_2$, or $C_3$ alkoxy;

m is 1 or 2; and n is 0, 1, or 2.

12. A compound having the formula wherein

A is cis or trans —CH═CH—;

B is absent;

$R_1$ represents an aromatic substituent which may contain a heteroatom and is a single ring, wherein $R_1$ is optionally substituted, wherein said substituents are selected from the group consisting of: hydrogen, halogen, amino, nitro, hydroxyl, alkoxy, alkyl, acyl and pyridyl, and said substitution may occur at any of the ortho, meta, or para positions;

$R_2$ and $R_3$ are both halogen;

m is 1 and n is 1.

13. A compound of claim 12 in which any one of the following conditions is met for $R_1$ and A:

$R_1$ is ortho-methoxyphenyl and A is trans —CH═CH—;

$R_1$ is meta-methoxyphenyl and A is trans —CH═CH—;

$R_1$ is para-methoxyphenyl and A is trans —CH═CH—;

$R_1$ is ortho-hydroxyphenyl and A is trans —CH═CH—;

$R_1$ is ortho-hydroxyphenyl and A is trans —CH═CH—;

$R_1$ is para-hydroxyphenyl and A is trans —CH═CH—;

$R_1$ is ortho-nitrophenyl and A is trans —CH═CH—;

$R_1$ is meta-nitrophenyl and A is trans —CH═CH—;

$R_1$ is para-nitrophenyl and A is trans —CH═CH—;

$R_1$ is ortho-aminophenyl and A is trans —CH═CH—;

$R_1$ is meta-aminophenyl and A is trans —CH═CH—;

$R_1$ is phenyl and A is trans —CH═CH—; or $R_1$ is phenyl and A is cis —CH═CH—.

14. A compound of claim 12 wherein R₁ is and A is trans —CH=CH—; or
R₁ is and A is trans —CH=CH—.

15. A compound of claim 6, wherein R₁ is and A is trans —CH=CH—.

* * * * *